(12) United States Patent
Gerner et al.

(10) Patent No.: US 6,678,051 B2
(45) Date of Patent: Jan. 13, 2004

(54) FLOW CELLS UTILIZING PHOTOMETRIC TECHNIQUES

(75) Inventors: Yuri Gerner, Mendota Heights, MN (US); Carl W. Sims, St. Paul, MN (US); Thomas Thielen, Plymouth, MN (US)

(73) Assignee: Systec, Inc., New Brighton, MN (US)

( * ) Notice: Subject to any disclaimer, the term of this patent is extended or adjusted under 35 U.S.C. 154(b) by 297 days.

(21) Appl. No.: 09/765,497

(22) Filed: Jan. 18, 2001

(65) Prior Publication Data
US 2002/0171836 A1 Nov. 21, 2002

(51) Int. Cl.[7] .......................... G01N 21/00; G01N 1/10
(52) U.S. Cl. .......................... 356/436; 356/246
(58) Field of Search .......................... 250/573, 576, 250/239, 227.25; 356/436, 246; 422/104, 102, 82.05, 82.09; 385/12, 125

(56) References Cited

U.S. PATENT DOCUMENTS

| | | | |
|---|---|---|---|
| 3,795,450 A | 3/1974 | Munk | |
| 3,954,341 A | 5/1976 | Uffenheimer | |
| 4,009,382 A | * 2/1977 | Nath | ............ 362/582 |
| 4,260,257 A | 4/1981 | Neeley et al. | |
| 4,530,569 A | 7/1985 | Squire | |
| 4,571,078 A | 2/1986 | Capps, II | |
| 4,575,424 A | 3/1986 | Allington et al. | |
| 4,754,009 A | 6/1988 | Squire | |
| 4,802,768 A | * 2/1989 | Gifford et al. | ............ 356/417 |
| 4,816,123 A | 3/1989 | Ogan et al. | |
| 4,867,559 A | 9/1989 | Bach | |
| 4,886,356 A | 12/1989 | Paradis | |
| 4,889,611 A | 12/1989 | Blough, Jr. | |
| 4,973,142 A | 11/1990 | Squire | |
| 4,975,505 A | 12/1990 | Squire | |
| 4,977,025 A | 12/1990 | Squire | |
| 4,999,248 A | 3/1991 | Squire | |
| 5,000,547 A | 3/1991 | Squire | |
| 5,006,382 A | 4/1991 | Squire | |
| 5,061,024 A | 10/1991 | Keys | |
| 5,076,659 A | 12/1991 | Bekiarian et al. | |
| 5,120,129 A | 6/1992 | Farquharson et al. | |
| 5,140,169 A | 8/1992 | Evens et al. | |
| 5,153,679 A | 10/1992 | Gilby | |
| 5,184,192 A | 2/1993 | Gilby et al. | |
| 5,267,341 A | 11/1993 | Shearin | |
| 5,404,217 A | 4/1995 | Janik et al. | |
| 5,416,879 A | 5/1995 | Liu | |
| 5,444,807 A | 8/1995 | Liu | |
| 5,570,447 A | 10/1996 | Liu | |
| 5,604,587 A | 2/1997 | Che et al. | |
| 5,608,517 A | 3/1997 | Munk | |
| 5,822,067 A | 10/1998 | Yanik | |
| 5,847,835 A | 12/1998 | Fukunaga | |
| 5,854,863 A | 12/1998 | Erb et al. | |
| 5,883,721 A | 3/1999 | Gilby et al. | |
| 5,917,606 A | 6/1999 | Kaltenbach | |
| 6,011,882 A | 1/2000 | Dasgupta et al. | |
| 6,016,372 A | 1/2000 | Fein et al. | |
| 6,020,207 A | 2/2000 | Liu | |
| 6,188,813 B1 | * 2/2001 | Dourdeville et al. | ............ 385/12 |
| 6,542,231 B1 | * 4/2003 | Garrett | ............ 356/246 |

* cited by examiner

*Primary Examiner*—Zandra V. Smith
*Assistant Examiner*—Gordon J Stock, Jr.
(74) *Attorney, Agent, or Firm*—Haugen Law Fim PLLP

(57) ABSTRACT

A flow cell for transporting fluid in a radiant energy field includes a cell structure having an open channel, and one or more end caps having a protrusion extending therefrom, wherein the protrusion may be inserted into the open channel to create a fluid seal. In a particular embodiment, the end caps include open channels for transporting fluid and radiant energy therethrough, and the open channel in the cell structure includes an efficient radiant energy transmission lining that is spaced from the end cap protrusions, thereby forming a gap volume in the flow cell open channel, which gap volume may be calibrated such that radiant energy losses may be standardized in respective flow cells transporting fluids having various indexes of refraction.

19 Claims, 3 Drawing Sheets

FLOW CELLS UTILIZING PHOTOMETRIC TECHNIQUES

FIELD OF THE INVENTION

The present invention relates to flow cells generally, and more particularly to radiant energy flow cells for use in various analytical chemistry applications, such as spectrophotometry. This invention also relates to methods for fabricating such flow cells.

BACKGROUND OF THE INVENTION

Numerous devices have been designed and implemented for use in preparing and testing samples in various environments, particularly in analytical chemistry applications. One such device is a flow cell, which may be used to transport samples to and through analytical instruments such as spectrophotometers for analysis purposes. Flow cells have typically been utilized to transport liquid samples, but other flowable sample types have also been implemented.

Most commonly, flow cells have been implemented to transport sample solutions through a volume disposed between a radiant energy source and an energy detector, which detector measures the relevant energy absorption or transmission through the sample solution. An example of such a detector is a spectrophotometer. Various analytical instruments then interpret the resultant energy "fingerprints" or transmitted vs. absorbed wavelengths to decipher sample constituents.

To efficiently pass the energy through the sample solution, however, the flow cell walls must have an index of refraction less than that of the sample solution to permit relatively long distance wave propagation. In previous flow cell configurations, the sample to be analyzed needed to be solvated in a fluid having a higher index of refraction than materials commonly used in flow cells. As a result, organic fluids were typically utilized as solvents in flow cell applications due to their relatively high index of refraction.

For several reasons, however, aqueous fluid carriers have been sought as a preferred alternative to such organic fluids. To implement a flow cell system utilizing an aqueous fluid, a material having an index of refraction less than that of water is needed for the respective flow cells. One such material is a perflourinated copolymer developed by DuPont of Wilmington, Del., under the trade name Teflon AF™. Thus, analytical flow cells preferably include a layer of Teflon AF™ or other low index of refraction material to allow efficient radiant energy propagation in spectrophotometry and photometry applications.

Most flow cells in use today generally do not embody efficient and reliable designs. Many employ multi-sectional, multi-directional tubes which may cause "dead flow" zones, and may introduce an increased risk of fluid leakage. Other flow cell designs are undesirably complex, are difficult to implement in current analytical instrument geometries, or are excessively expensive to produce.

Accordingly, it is a principle object of the present invention to provide an improved means for exposing a sample solution to a radiant energy field used for analyzing sample composition.

It is a further object of the present invention to provide an improved flow cell design yielding desired sample solution flow characteristics.

It is another object of the present invention to provide a flared-tube flow cell design which reduces flow turbulence through the flow cell.

It is a yet further object of the present invention to provide a flow cell having a calibrated gap volume for standardizing radiant energy losses among various fluids flowing through a radiant energy field.

It is a still further object of the present invention to provide an improved flow cell including an end cap having a substantially conical frustum portion which engages the flow cell to form a sealed fluid passageway.

It is a further object of the present invention to provide an improved flow cell having end caps which are sized and configured to form high-pressure fluid seals when engaged with a flow cell body.

It is a yet further object of the present invention to provide end caps for a flow cell, wherein the end caps include passageways for fluid and radiant energy transport, and improved sealing means for sealing relationship with the flow cell.

It is a yet further object of the present invention to provide a flow cell having improved radiant energy transmission characteristics.

It is a still further object of the present invention to provide an improved flow cell for use in HPLC applications.

It is a yet further object of the present invention to provide a method for fabricating flow cells having improved sealing and fluid transport characteristics.

It is a further object of the present invention to provide a method for fabricating flow cells utilizing extruded tubing.

SUMMARY OF THE INVENTION

By means of the present invention, an improved flow cell is contemplated for use in transporting sample fluids in radiant energy fields. Such a flow cell introduces a structure for improved fluid sealing and fluid flow characteristics.

One embodiment of the flow cell of the present invention preferably includes a cell structure having a first open channel therein which forms a continuous passageway through the cell structure. Attached to the flow cell is at least one end cap that is sealingly engagable with the cell structure. The end cap preferably includes a substantially conical frustum portion extending outwardly therefrom. When assembled, the conical frustum portion preferably extends at least partially into the first open channel.

The first open channel is preferably clad with one or more layers. Preferably, the innermost layer is a low index of refraction material such as Teflon AF™. A second layer preferably comprising PEEK substantially concentrically surrounds the first Teflon AF™ layer. Preferably, a third layer comprising FEP substantially concentrically surrounds the PEEK layer, and is in intimate contact with an outer wall of the first open channel. As assembled, the conical frustum portion of the end caps preferably displace a portion of the FEP layer against the first open channel wall, thereby forming a fluid-tight seal between the FEP layer and the conical frustum portions.

Preferably, the end caps include one or more open channels for transporting the sample fluid and the radiant energy. In preferred embodiments, the radiant energy channels are in substantial alignment with the first open channel within the cell structure. The radiant energy channels and the fluid channels preferably merge such that the radiant energy may pass through the sample fluid.

At least one end of the innermost layer is preferably flared outwardly to more efficiently transport the radiant energy and sample fluid. The flared portion of the innermost layer is calibrated so that an internal dimension of the innermost layer may be reduced without significant radiant energy losses, and further enables a reduction in fluid flow turbulence. Such reduced flow turbulence increases the reliability of photometric sample analysis.

In another aspect of the present invention, a gap volume is provided between the first open channel within the cell structure and fluid channels within respective end caps. The gap volume is preferably and adjustably calibrated to define an appropriate volume such that radiant energy losses among various fluids having distinct indexes of refraction may be standardized.

The present invention also contemplates a method for determining sample composition through radiant energy interaction with the sample fluid utilizing the structural elements described above.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
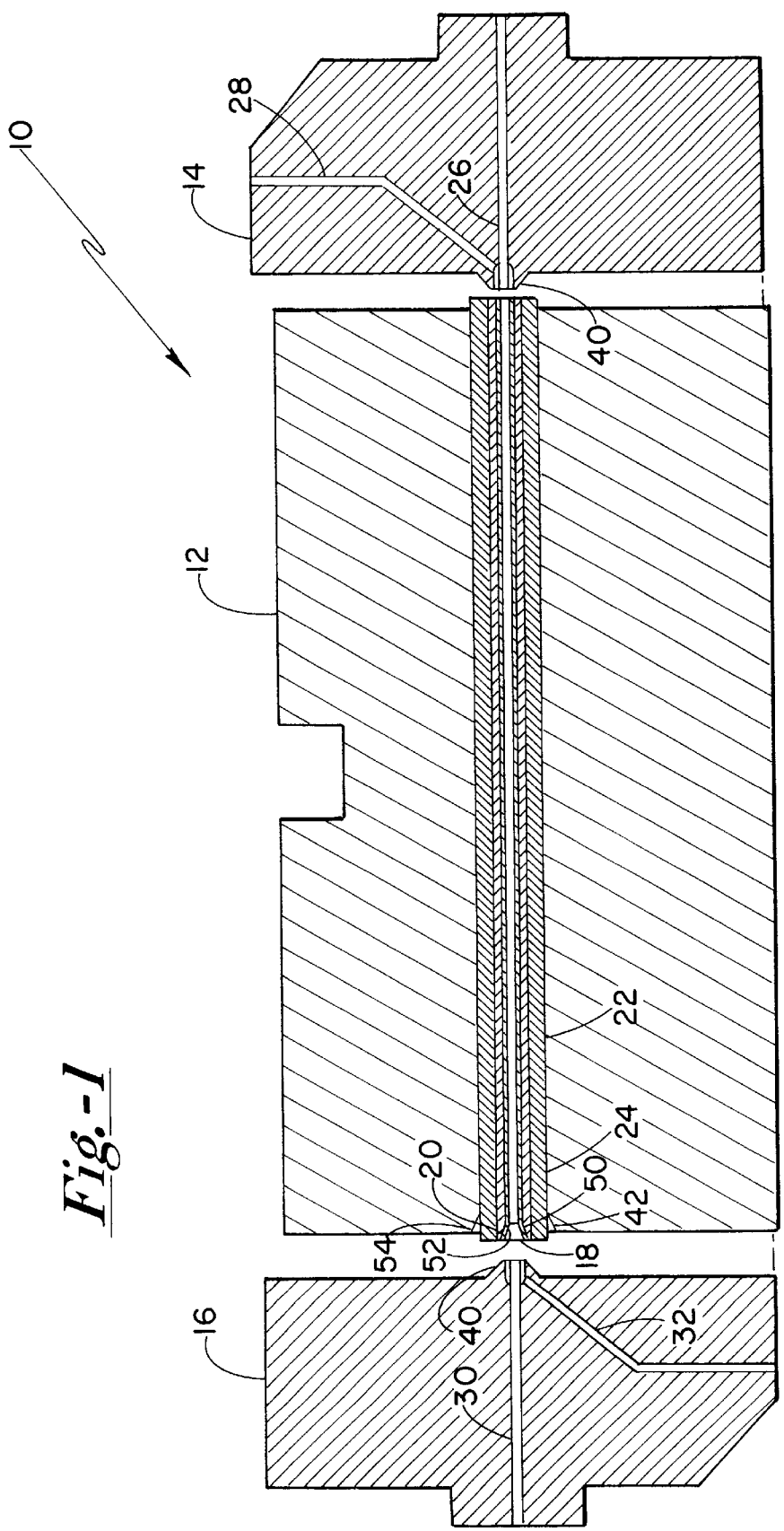
FIG. 1 is a partially exploded cross-sectional view of a flow cell of the present invention.

Referring now by characters of reference to the drawings, and first to FIG. 1, a partially exploded cross-sectional view of a flow cell 10 of the present invention is shown. Flow cell 10 includes cell body 12, and first and second end caps 14, 16 respectively. Cell body 12 preferably includes a first open channel 18 extending therethrough to form a continuous passageway through a length of the cell body. One or more distinct material layers preferably surround open channel 18. Such layers preferably concentrically surround open channel 18, so as to form concentric tubes, an inside diameter of the innermost tube thereby defining open channel 18. The concentricity of respective layers is preferably tightly controlled.

In a preferred embodiment, a first layer 20 of relatively low index of refraction material concentrically surrounds open channel 18. A low refractive index material is desired for use in the first layer 20 so that radiant energy passing through sample fluids in channel 18 is able to propagate over relatively long distances with little deterioration. Flow cell applications employing spectrophotometers or other instruments to analyze fluid composition require that the tube walls within which the fluid and radiant energy pass must possess an index of refraction less than that of the fluid to allow efficient propagation of the radiant energy (by a phenomenon known as full internal reflection). Thus, if water is to be used as a base fluid for sample analysis in high-performance liquid chromatography or other analytical chemistry applications utilizing flow cells where internal walls are in contact with the fluid, the internal wall material preferably has an index of refraction less than that of water.

Such an application is contemplated for the present invention. An example of such a low refractive index material is Teflon AF™, developed and sold by Dupont, Inc. of Wilmington, Del. At present, Teflon AF™ is the most preferred material for use in the first layer 20 because it is the only material readily available that has an index of refraction lower than that of water or other solvents used in sample analysis, and because it is chemically compatible with most of these solvents. Thus, first layer 20 preferably comprises Teflon AF™. Preferably, an inner surface of such first layer 20 is relatively free of imperfections, and any imperfections present are preferably smaller than the radiant energy wave length.

Preferably, first layer 20 is sufficiently thick to prevent radiant energy losses caused by radiant energy penetration through the first layer. As radiant energy is transported through first open channel 18 of cell body 12, the radiant energy penetrates first layer 20 as an evanescent wave, the intensity of which decays exponentially with the depth of first layer 20. For efficient radiant energy transmission through open channel 18, the thickness "T" of first layer 20 should be larger than the penetration depth "δ" of the radiant energy incident thereon. Such depth is given by the following equation, where $n_T$ is the refractive index of first layer 20, $n_i$ is the refractive index of the sample fluid, $\lambda_i$ is the wavelength of the incident radiant energy, and i is the radiant energy angle of incidence into channel 18.

$$\delta = \left( \frac{2\pi}{\lambda_i} \sqrt{\frac{\sin^2(i)}{\left(\frac{n_T}{n_i}\right)^2} - 1} \right)^{-1}$$

In preferred embodiments of the invention, first layer 20 has a thickness of at least two wavelengths of the respective radiant energy passing through open channel 18. Most preferably, first layer 20 is at least 15 μm thick.

In some embodiments, first layer 20 is tubular in form, and preferably forms the boundary defining a course of travel for fluid and radiant energy through cell body 12.

In preferred embodiments of the present invention, second and third layers 22, 24, respectively, are disposed concentrically around first layer 20. Second and third layers 22, 24 are preferably polymeric materials, and are preferably tubular in form. In a particularly preferred embodiment, second layer 22 is PEEK, and third layer 24 is FEP. As shown in FIG. 1, second layer 22 is interposed between first layer 20 and third layer 24, and may be in intimate contact with both first layer 20 and third layer 24. In preferred embodiments, clearance between first, second, and third layers, respectively is maintained at no greater than 2% of an inner dimension of channel 18.

In preferred embodiments and as illustrated in FIG. 1, third layer 24 is substantially concentrically surrounded by the remainder of cell body 12, which is preferably a rigid, non-corrosive material such as stainless steel. Other materials, however, may be used in place of the exemplary stainless steel.

First and second end caps 14, 16 preferably include at least one open channel extending therethrough. Second open channel 26 is preferably disposed in first end cap 14, and is preferably in alignment with first open channel 18. Similarly, a third open channel 30 is disposed in end cap 16, and is in alignment with channel 18. As shown in FIG. 1, second and third open channels 26 and 30 preferably extend through an entire length of end caps 14 and 16 respectively. Preferably, channels 26, 30 are utilized for transporting radiant energy through flow cell 10, and are desirably disposed in a single plane to eliminate measurement errors which could result from various angled reflection characteristics. In preferred embodiments, channels 26, 30 are fabricated from a material efficient in transporting radiant energy, such as, for example, fiber optic material. A particularly preferred material for use in channels 26, 30 is a quartz fiber optic. Preferably, then, channels 26, 30 are in a direct, straight-line alignment with channel 18. Most preferably, first, second, and third layers 20, 22, 24, respectively, are substantially in concentric alignment with channels 26, 30, and have an offset of no greater than 5% of an inner dimension of channel 18.

In preferred embodiments of the present invention, a fluid channel 28 is disposed in end cap 14, and extends from said second channel 26 to an exterior surface of end cap 14. As shown in FIG. 1, fluid channel 28 preferably extends through an entire dimension of end cap 14 such that fluid may flow between an exterior surface of end cap 14 and open channel 18 through fluid channel 28. Walls defining fluid channel 28 may be the same material as end cap 14, or may be lined or coated with a different material that may be desired for particular applications.

In the embodiment illustrated in FIG. 1, end cap 16 is preferably similar to end cap 14. End cap 16 preferably includes a third open channel 30 extending therethrough in a plane coincident with a plane associated with open channel 18. Furthermore, end cap 16 preferably includes a fluid channel 32 extending from such third open channel 30 to an exterior surface of end cap 16, thereby providing a flow duct for fluid to pass between open channel 18 and the exterior of end cap 16.

A preferred feature of the embodiment depicted in FIG. 1 is the protrusion 40 extending from the respective end caps 14, 16. Protrusions 40 are adapted to be received in cell body 12 such that a fluid seal is formed at an interface between the cell body and the respective end caps 14, 16. Second and third open channels 26, 30, respectively, preferably extend through protrusions 40 such that respective openings to the second and third open channels are disposed in respective outer surfaces of the protrusions 40. In a particularly preferred embodiment of the present invention, protrusions 40 substantially form conical frustum portions extending from respective end caps 14, 16. As shown in FIG. 1, second and third open channels 26, 30 preferably extend through the frustum portions of said protrusions 40.

Figure 2:
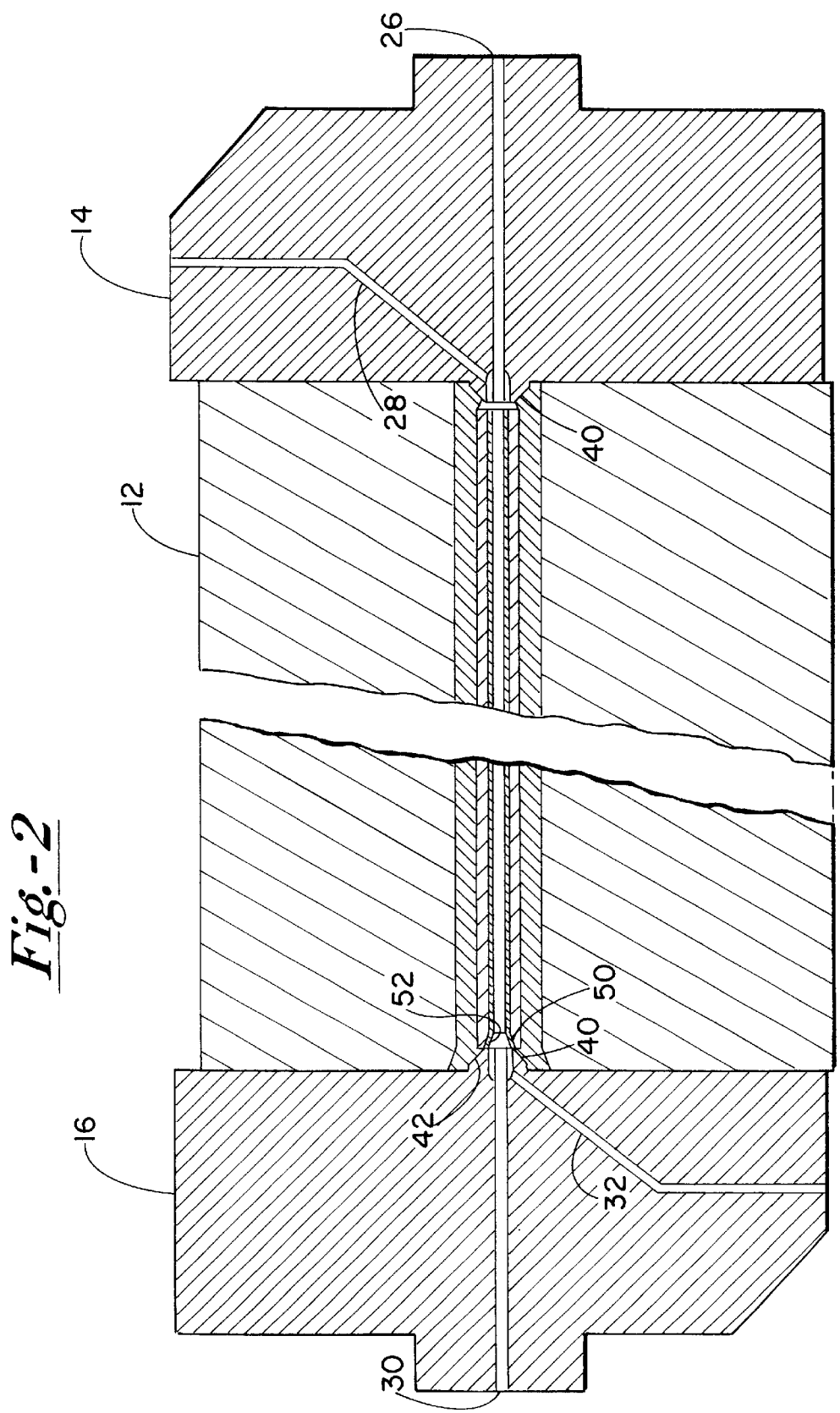
FIG. 2 is a cross-sectional view of the flow cell shown in FIG. 1.

The preferred conical frustum shape provides desired fluid sealing characteristics at end cap/cell body interfaces. As shown in FIG. 2, and more clearly in FIG. 3, a section of first layer 20 is flared outwardly. The flared section of first layer 20 is preferably formed by inserting a highly polished heated conical structure into channel 18 defined by first layer 20. In embodiments wherein first layer 20 comprises Teflon AF™, the conical structure is heated to a temperature near a Teflon AF™ glass transition point (240° C.), but under the melting point for Teflon AF™. The heated conical structure therefore forms a portion of first layer 20 to an exterior surface shape of the conical structure.

In some embodiments, first layer 20 is flared to alter an inner dimension of open channel 18 such that fluid may pass to and from open channel 18 more efficiently. The flared section of first layer 20 reduces fluid flow turbulence in channel 18, thereby providing a higher degree of laminar flow. Since fluid flow turbulence causes dispersion in radiant energy passing through the fluid, a reduction in flow turbulence desirably reduces "scattering noise" in photometric analyses of radiant energy transmission, and therefore results in increased spectrophotometric accuracy.

Preferably, an end section 50 of first layer 20 is flared outwardly such that an inner dimension of open channel 18 at end section 50 is substantially equal to a respective inner dimension of open channel 30. By outwardly flaring a portion of first layer 20, an inner dimension of open channel 18 may be correspondingly reduced. Such reduction in the internal dimension of open channel 18 correspondingly reduces an inner dimension of first layer 20, which allows a smaller internal volume of open channel 18, thereby reducing sample band spreading in the channel without significant reduction in radiant energy transmission through open channel 18. Furthermore, flared section 50 of first layer 20 enables the reduction of an internal dimension of first layer 20 to less than that of open channel 30 without significant radiant energy losses, due to the angle of inflection between open channel 30 and flared section 50 of channel 18. Such minimum radiant energy loss is possible so long as the flared portion angle combined with the radiant energy angle of incidence is smaller than a radiant energy acceptance angle e. Such an acceptance angle θ may be determined by the following relationship, where NA is the numerical aperture of channel 18, $n_f$ is the refractive index of the sample fluid, and $n_{fl}$ is the refractive index of the first layer.

$$\sin \theta = NA = \sqrt{n_f^2 - n_{fl}^2}$$

Outwardly flared section 50 of first layer 20 is preferably sealingly in intimate contact with a chamfered portion 52 of second layer 22.

Figure 3:
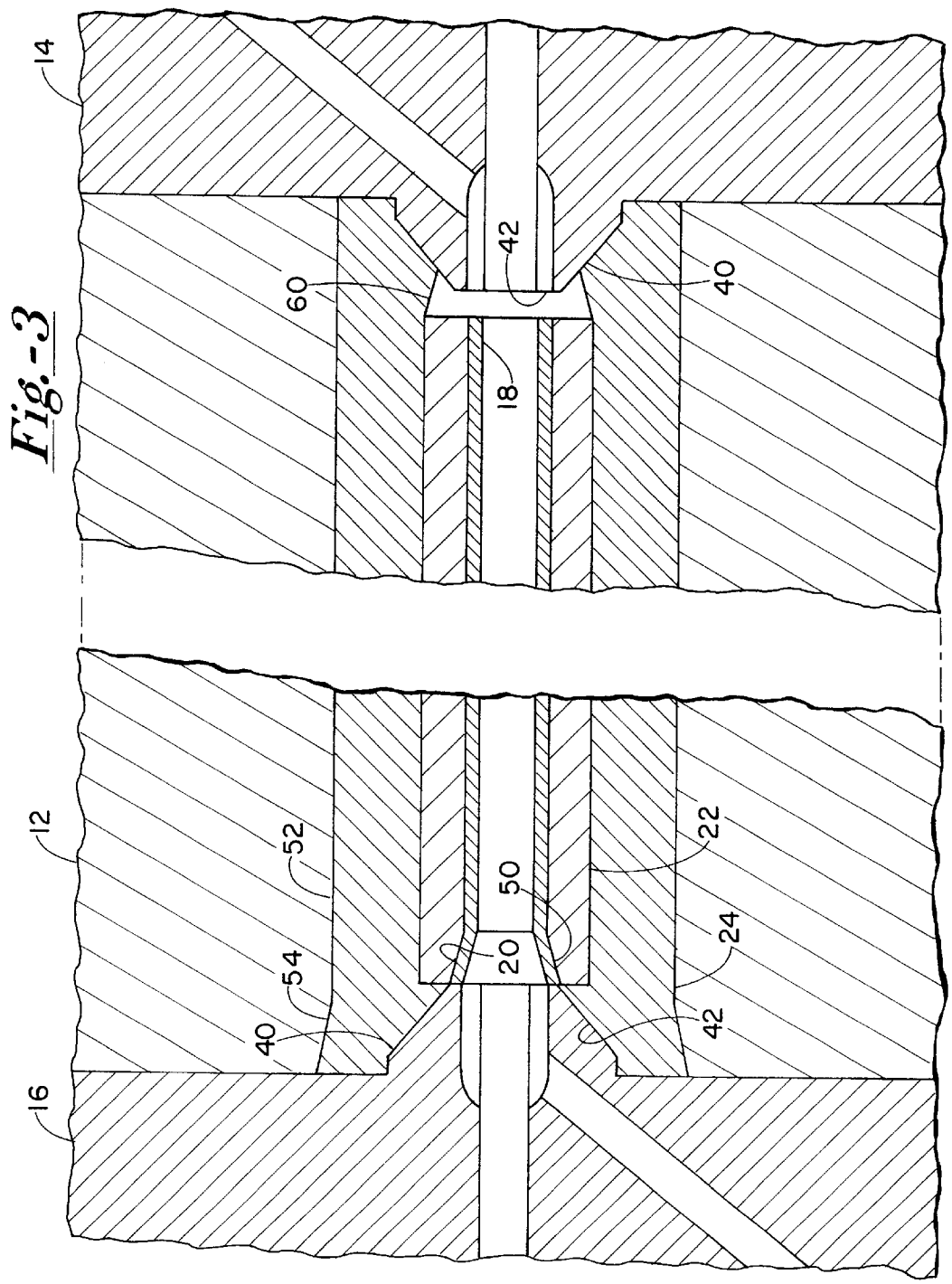
FIG. 3 is an enlarged cross-sectional view of the flow cell shown in FIG. 2.

As illustrated in FIG. 3, protrusion 40 preferably outwardly displaces a portion of third layer 24 against cell body 12. Such outward displacement creates a latent expansion force in compressed portion 54 of third layer 24. This expansion force preferably assists in securing protrusion 40 in place, and acts to form a fluid seal between protrusion 40 and third layer 24.

Protrusions 40 are illustrated in FIG. 3 as having a generally conical frustum shape, and extending substantially perpendicularly from respective end caps 14, 16. Such a conical frustum shape is preferred for providing desired alignment and sealing characteristics. Conical portions 42 of respective protrusions 40 preferably firmly seat against first layer 20 and displace a portion of the third layer when the respective end caps 14, 16 are assembled to cell body 12 to form flow cell 10. Such displacement provides a relatively high-pressure fluid seal between third layer 24 and protrusion 40. Such a high-pressure seal preferably withstands fluid pressure of up to 2000–3000 pounds per square inch. In addition, the engagement of frustum portions 42 in cell body 12 provides a high-pressure fluid seal at an interface between layers 22 and 24. Frustum portions 42 are preferably arranged to linearly align open channel 18 with respective second and third open channels 26, 30.

The flow cell of FIGS. 1–3 is preferably formed by providing the end caps as described above and a cell body having an open bore extending therethrough. A section of Teflon AF™ tubing is selected for use as the first layer within the open bore. The Teflon AF™ tube may be formed through an extrusion process or any other process that effectively creates such tubing. The Teflon AF™ tube section is then preferably positioned within a section of PEEK tubing, which PEEK tubing forms the second layer within the open bore. In preferred embodiments, the PEEK tube section is in intimate contact with the Teflon AF™ tube. An inner surface of at least one end portion of the PEEK tube section is preferably chamfered outwardly to form a generally conical end portion. A heated cone is subsequently inserted a desired distance into a corresponding portion of the Teflon AF™ tube to flare such Teflon AF™ tube section outwardly against the chamfered portion of the outwardly-disposed PEEK tube. The combination PEEK/Teflon AF™ (PT) tube section is then cut to a precision length in such a manner so as to form a clean cut edge having little or no edge distortions or burrs.

Preferably, a section of FEP tubing is cut to a length which is longer than the PT tube section, and the PT tube section is inserted therein, thereby forming a multiple-layered tube section. The multi-layered tube section is then inserted into the open bore in the cell body. In a preferred embodiment of the present invention, the FEP tube section is heated to a point at which the material is somewhat pliable. The heated tube section is then stretched and thinned, and pulled through the open bore of the cell body, and subsequently cut to a desired length. Once the FEP section has cooled, the PT tube section is inserted into the FEP tube section to thereby form a multi-layered tube assembly within the cell body. Preferably, the PT tube section is friction fit within the FEP tube section.

Once the multi-layered tube assembly positioned within the cell body, the respective end caps are engaged to the cell body such that the protrusions extend at least partially into the open bore. As shown in FIGS. 2 and 3, the protrusions 40 displace a portion of the FEP layer against the cell body, thereby forming a fluid-tight seal between respective protrusions 40 and the FEP layer 24, and between PEEK layer 22 and FEP layer 24. Furthermore, the multi-layered tube assembly is effectively secured between respective end caps 14, 16, and within cell body 40. Preferably, open channel 18, defined by an inner dimension of the Teflon AF™ is in alignment with respective second and third open channels 26, 30 to allow efficient fluid and radiant energy flow through flow cell 10.

As shown in FIG. 3, a gap 60 is preferably left between conical frustum portion 42 of end cap 14 and a respective end of channel 18. In operation, sample fluid fills gap 60, thereby resulting in calculatable radiant energy losses as the radiant energy passes through the fluid-filled gap which is absent the efficient radiant energy transmitting first layer 20. Thus, radiant energy entering gap 60 is allowed to disperse throughout the volume defined by gap 60, causing partial diffusion or loss of the radiant energy. Fluids having relatively higher refractive indexes result in greater degree of radiant energy loss as compared to fluids having relatively lower refractive indexes. Such radiant energy losses may be calculated by the following relationship:

$$E = -10 \log \left[1 - \left(a \cdot \frac{NA}{D \cdot n_f}\right)\right]$$

where "E" is the radiant energy loss, "a" is the distance between conical frustum portion 42 of end cap 14 and channel 18, defined as gap 60, NA is the numerical aperture of channel 18, D is an internal dimension of channel 18, and $n_f$ is the refractive index of the respective sample fluid. Using such a relationship, a designer of the present invention may select an appropriate gap 60 dimension to offset radiant energy losses for in the first open channel 18 various fluids having different refractive indexes, thereby standardizing such energy losses among the various fluids. Such energy losses inevitably occur in every real open channel 18 due to inherent wall surface imperfections and result in a greater degree of radiant energy loss for fluids having relatively lower refractive indexes as compared to fluids having relatively higher refractive indexes. A typical range for gap 60/channel 18 inner dimension ratio (a/D) is between about 0.1 and about 1.0.

The invention has been described herein in considerable detail in order to comply with the Patent Statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A flow cell for transporting fluid in a radiant energy field, comprising:
    (a) a cell structure having a first open channel therein, said first open channel forming a continuous passageway through said cell structure, and multiple distinct layers disposed substantially concentrically about said first open channel, including a first inner layer, a second layer disposed substantially concentrically around said first inner layer, and a third layer disposed substantially concentrically around said second layer;
    (b) a first end cap that is sealingly engageable with a first end of said cell structure, said first end cap having a first protrusion extending at least partially into said first open channel in said cell structure, and a second open channel substantially aligned with said first open channel to extend the continuous passageway through said first end cap; and
    (c) a second end cap disposed on, and sealingly engageable with, a second end of said cell structure, said second end cap having a second protrusion extending at least partially into said first open channel, and a third open channel substantially aligned with said first open channel so as to extend the continuous passage way through said second end cap,
    wherein said first and second protrusions are shaped as conical frustums such that said first and second end caps, in combination, form a fluid seal in said flow cell, said conical frustum protrusions of said first and second end caps being positioned to displace respective portions of said third layer, thereby forming a fluid-tight seal between said third layer and said conical frustum protrusions.

2. A flow cell as in claim 1 wherein said second layer comprises PEEK.

3. A flow cell as in claim 1 wherein said third layer comprises PEP.

4. A flow cell as in claim 1 wherein said third layer is substantially concentrically surrounded by a remainder of said cell structure, the cell structure remainder comprising stainless steel.

5. A flow cell as in claim 1 wherein said first inner layer comprises a perfluorinated copolymer.

6. A flow cell as in claim wherein said first layer is formed through an extrusion process.

7. A flow cell as in claim 1 wherein an end portion of said first layer is flared outwardly.

8. A flow cell as in claim 1 wherein the fluid and radiant energy are directed through the continuous passageway such that the radiant energy coaxially passes through the fluid.

9. A flow cell as in claim 1 wherein said second end cap protrusion is displaced from respective ends of said first and second layers, whereby a predetermined gap volume is adjustably formed in said radiant energy field for fluid residence therein.

10. A flow cell as in claim 9 wherein said gap volume is selectively calibrated such that radiant energy losses may be standardized in respective flow cells transporting fluids having various indexes of refraction.

11. A method of determining sample composition through radiant energy interaction, comprising:
   (a) providing a cell body having an open bore extending therethrough;
   (b) providing multiple distinct layers of material lining said open bore including a first inner layer, a second layer disposed substantially concentrically around said first inner layer, and a third layer disposed substantially concentrically around said second layer;
   (c) attaching first and second end caps to said cell body, said end caps including protrusions extending therefrom, wherein said protrusions extend at least partially into said open bore in said cell body such that a fluid-tight seal is formed thereat, said protrusions being shaped as conical frustums and being positioned to displace respective portions of said third layer, thereby forming a fluid-tight seal between said third layer and said conical frustum protrusions, said end caps further including one or more open channels in substantial alignment with said open bore;
   (d) transporting sample fluid and radiant energy through said open bore such that the radiant energy passes through the sample fluid; and
   (e) receiving and interpreting the radiant energy that has passed through the sample fluid.

12. A method as in claim 11 wherein said first layer is a perfluorinated copolymer said second layer is PEEK said third layer is FEP.

13. A method as in claim 11 wherein said end caps each include a radiant energy tube comprising fiber optic material, and a sample fluid tube, said radiant energy tube and said sample fluid tube merging at or adjacent said open bore so that the radiant energy may pass through the sample fluid.

14. A method as in claim 13 wherein said radiant energy tube is in substantial alignment with said open bore.

15. A flow Cell for transporting fluid in a radiant energy field, comprising:
   (a) a cell structure having a first open channel therein, said first open channel forming a continuous passageway through said cell structure;
   (b) a first material layer disposed substantially concentrically about said first open channel;
   (c) a first end cap that is sealingly engageable with a first end of said cell structure, said first end cap having a second open channel substantially aligned with said first open channel to extend the continuous passageway through said first end cap; and
   (d) a second end cap sealingly engageable with a second end of said cell structure, said second end cap having a third open channel substantially aligned with said first open channel so as to extend the continuous passageway through said second end cap, said second end cap being adjustably positioned in calibrated increments with respect to said first open channel so as to create a predetermined adjustable gap volume in between said second end cap and said first material layer and within said for fluid residence therein, such that radiant energy losses may be standardized in respective flow cells transporting fluids having various indexes of refraction.

16. A flow cell as in claim 15 wherein said first material layer comprises a perfluorinated copolymer.

17. A flow cell as in claim 15 wherein said first end cap includes a first protrusion extending at least partially into said open channel.

18. A flow cell as in claim 17 wherein said second end cap includes a protrusion extending at least partially into said first open channel.

19. A flow cell as in claim 18 wherein said first and second end caps, in combination, form a fluid seal in said flow cell.

* * * * *

UNITED STATES PATENT AND TRADEMARK OFFICE
CERTIFICATE OF CORRECTION

PATENT NO.     : 6,678,051 B2                                    Page 1 of 1
DATED          : January 13, 2004
INVENTOR(S)    : Yuri Gerner et al.

It is certified that error appears in the above-identified patent and that said Letters Patent is hereby corrected as shown below:

<u>Column 8,</u>
Line 45, replace "PEP" with -- FEP --
Line 52, after the word "claim", add -- 1 --

<u>Column 9,</u>
Line 28, after the word "copolymer", please add -- , --

<u>Column 10,</u>
Line 23, after the word "said", please add -- radiant energy field --

Signed and Sealed this

Twenty-seventh Day of April, 2004

JON W. DUDAS
*Acting Director of the United States Patent and Trademark Office*